United States Patent [19]
Yomtov et al.

[11] Patent Number: 5,522,850
[45] Date of Patent: Jun. 4, 1996

[54] DEFIBRILLATION AND METHOD FOR CARDIOVERTING A HEART AND STORING RELATED ACTIVITY DATA

[75] Inventors: Barry M. Yomtov, Issaquah; David P. Finch, Bothell, both of Wash.

[73] Assignee: InControl, Inc., Redmond, Wash.

[21] Appl. No.: 264,319

[22] Filed: Jun. 23, 1994

[51] Int. Cl.$^6$ ............................................. A61N 1/39
[52] U.S. Cl. .................................................... 607/5
[58] Field of Search ................................. 607/5-8

[56] References Cited

U.S. PATENT DOCUMENTS

| | | | |
|---|---|---|---|
| 4,223,678 | 9/1980 | Langer et al. | 128/419 |
| 4,295,474 | 10/1981 | Fischell | 607/5 |
| 4,572,191 | 2/1986 | Mirowski et al. | 607/7 |
| 5,366,486 | 11/1994 | Zipes et al. | 607/5 |

FOREIGN PATENT DOCUMENTS

| | | | |
|---|---|---|---|
| 0653835 | 11/1992 | Australia | 607/5 |
| 0522693 | 1/1993 | European Pat. Off. | 607/5 |

OTHER PUBLICATIONS

*Advances in Third Generation ICD Therapy*, Hook et al., Cardio, Nov., 1991, pp. 66–72.

*Primary Examiner*—William E. Kamm
*Attorney, Agent, or Firm*—Richard O. Gray, Jr.

[57] ABSTRACT

An implantable atrial defibrillator applies cardioverting electrical energy to the atria of a human heart in response to detection of an atrial fibrillation episode and stores selected data associated with the detected atrial fibrillation episode. The atrial defibrillator includes a cardiovertor which provides successive applications of cardioverting electrical energy to the atria of the heart until one of the pulses successfully cardioverts the atria. A memory system stores selected heart activity data in connection with the detected episode including heart activity data related to initial detection of the atrial fibrillation episode and heart activity data occurring from before and until after the application of the cardioverting electrical energy which successfully cardioverts the atria of the heart.

14 Claims, 2 Drawing Sheets

DEFIBRILLATION AND METHOD FOR CARDIOVERTING A HEART AND STORING RELATED ACTIVITY DATA

BACKGROUND OF THE INVENTION

The present invention generally relates to an atrial defibrillator which detects an atrial fibrillation episode and responsive to such detection, applies cardioverting electrical energy to the atria of a human heart. The present invention more particularly relates to such an atrial defibrillator which further selectively stores heart activity data related to the detection of the atrial fibrillation episode. The selectively stored data includes data relating to the initial detection of the atrial fibrillation episode and data relating to the successful cardioversion of the atria. The selectively stored data may further include data relating to a synchronization protocol implemented by the atrial defibrillator immediately prior to the successful cardioversion of the atria.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has precluded these defibrillators from becoming a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

An improved atrial defibrillator which does provide automatic operation is fully disclosed in U.S. Pat. No. 5,282,837 entitled IMPROVED ATRIAL DEFIBRILLATOR AND METHOD and which issued on Feb. 1, 1994 in the names of John M. Adams and Clifton A. Alferness. This patent is assigned to the assignee of the present invention and is incorporated herein by reference.

In addition to being automatic in operation, the atrial defibrillator of the above-referenced patent includes further features to assure the safe operation of the device. For example, to assure that the cardioverting electrical energy is not applied during the T wave vulnerable period of the heart, the atrial defibrillator provides R wave detection of increased reliability which is utilized to advantage in synchronizing the delivery of the cardioverting electrical energy to the atria with an R wave of the heart. Further, as another feature, an electrode system is utilized which minimizes the amount of energy that is applied to the ventricles during the cardioversion of the atria. This is achieved by locating the cardioverting electrodes in or near the heart to provide a cardioverting energy path which confines substantially all of the cardioverting electrical energy to the atria of the heart. This further reduces the risk of inducing ventricular fibrillation during the delivery of the cardioverting electrical energy to the atria of the heart.

Further improvements directed to the safe operation of an implantable automatic atrial defibrillator are described in U.S. Pat. No. 5,207,219 which issued on May 4, 1993 for ATRIAL DEFIBRILLATOR AND METHOD FOR PROVIDING INTERVAL TIMING PRIOR TO CARDIOVERSION and which is also assigned to the assignee of the present invention and incorporated herein by reference. The atrial defibrillator there disclosed provides an answer to the observation that during episodes of atrial fibrillation, the cardiac rate increases to a high rate and/or becomes extremely variable. At high or variable cardiac rates, the R wave of a cardiac cycle may become closely spaced from the T wave of the immediately preceding cardiac cycle. This creates a condition known in the art as an "R on T" condition which is believed to contribute to induced ventricular fibrillation if the atria are cardioverted in synchronism with the R wave close to the preceding T wave. In order to prevent cardioversion of the atria during an R on T condition, the atrial defibrillator described in U.S. Pat. No. 5,207,219 detects for a cardiac interval longer than a minimum interval prior to delivering the cardioverting electrical energy to the atria. This assures that the cardioverting electrical energy is not delivered during an R on T condition.

As can be seen from the foregoing, there is certain information related to atrial fibrillation and the cardioversion thereof from which the cardiologist would benefit. Such information includes activity of the heart during fibrillation to confirm proper operation of the atrial fibrillation detector, the activity of the heart prior to cardioversion and the activity of the heart from immediately prior to and ending after the deliverance of the cardioverting electrical energy to the atria to confirm that the application of the cardioverting electrical energy was synchronized with an R wave and not on a T wave and to also confirm that the cardioversion was successful by returning the heart to normal sinus rhythm. In order to provide such information, the implantable automatic atrial defibrillator would be required to store data, preferably representative of electrocardiograms of the heart.

The present invention provides such an implantable automatic atrial defibrillator capable of storing such information. More particularly, the atrial defibrillator of the present invention stores digital samples representative of selected electrocardiograms related to the detection of an atrial fibrillation episode and the successful cardioversion of the detected atrial fibrillation episode.

SUMMARY OF THE INVENTION

The present invention therefore provides an atrial defibrillator including cardioverting means for applying cardioverting electrical energy to the atria of the heart, sensing means for sensing electrical activity of the heart and generating heart activity data, storage means for storing the heart activity data generated by the sensing means during a discrete continuous time interval commencing before and ending after application of cardioverting electrical energy to the atria.

The present invention further provides a memory system for use in an atrial defibrillator which detects atrial fibrillation of the heart and applies cardioverting electrical energy to the atria when the atria are in need of cardioversion. The memory system stores data related to the detection of atrial fibrillation and the cardioversion of the atria and includes means for generating data associated with the activity of the heart, and means for storing data associated with the atria of the heart occurring during a discrete time period prior to detection of atrial fibrillation and for storing data associated with the activity of the heart occurring during a second discrete time period commencing before cardioversion of the heart and extending continuously until after cardioversion of the heart.

The present invention still further provides a memory system for use in an implantable atrial defibrillator which detects atrial fibrillation and applies cardioverting electrical energy to the atria when the atria are in need of cardioversion. The memory system stores data relating to the condition and cardioversion of the heart and includes a first temporary memory for initially storing data related to the condition and cardioversion of the heart, and a permanent memory for receiving data initially stored in the first temporary memory and for permanently storing the data initially stored in the first temporary memory.

The present invention further provides an implantable atrial defibrillator for applying cardioverting electrical energy to the atria of a human heart in response to detection of atrial fibrillation and for storing data associated with the detected atrial fibrillation of the heart. The atrial defibrillator includes detecting means for detecting activity of the heart, data generating means responsive to the detecting means for generating heart activity data, and atrial fibrillation detecting means responsive to detected activity of the heart for detecting atrial fibrillation of the heart. The atrial defibrillator further includes cardioverting means responsive to the detection of atrial fibrillation for providing successive applications of cardioverting electrical energy to the atria of the heart, and memory means for storing selected data of the heart activity data. The selected data includes initial heart activity data related to initial detection of the atrial fibrillation and heart activity data related to the application of cardioverting electrical energy to the atria. The data related to the application of the cardioverting electrical energy to the atria is heart activity data related only to a last one of the applications of cardioverting electrical energy to the atria of the heart.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
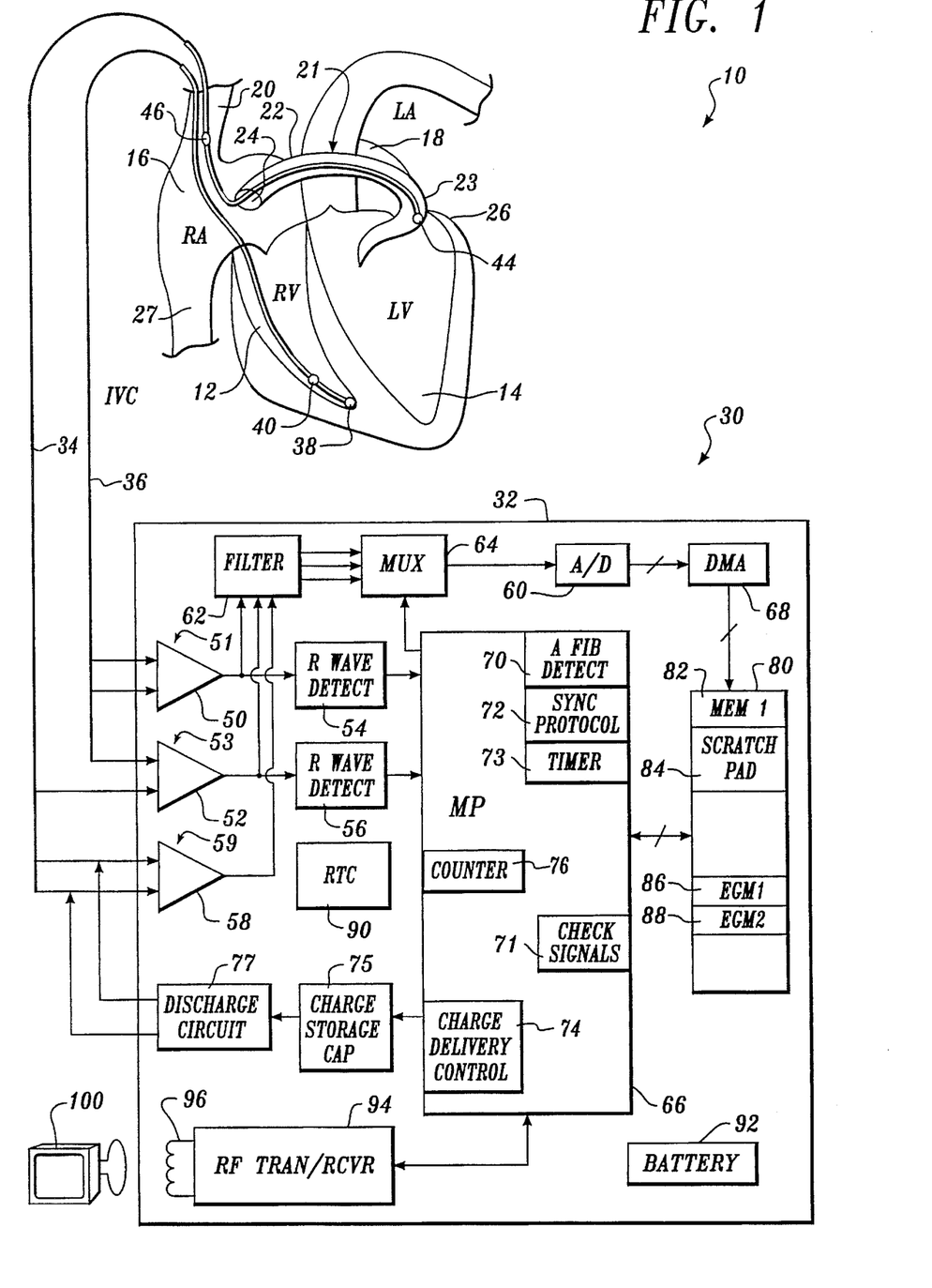
FIG. 1 is a schematic block diagram of a fully implantable atrial defibrillator embodying the present invention.

Referring now to FIG. 1, it illustrates an implantable automatic atrial defibrillator 30 embodying the present invention. Basically, the atrial defibrillator 30 will automatically determine when the atria 16 and 18 are in fibrillation and then automatically apply cardioverting electrical energy to the atria to arrest the fibrillation episode when it is safe to apply such energy. In the process of cardioverting the atria 16 and 18, the atrial defibrillator 30 stores in a memory 80 digital samples of electrocardiograms of the heart occurring during two distinct time periods.

The first time period for which such samples are stored is the last three second time period of an eight second acquisition time period. During this eight second acquisition time period, electrocardiogram digital samples are stored in a memory portion 82 (MEM 1) for subsequent use in determining if the atria of the heart are in fibrillation. If it is determined during the processing of the digital samples stored in memory portion 82 that the atria are in fibrillation and thus in need of cardioversion, the electrocardiogram samples for the last three seconds of the acquisition period are moved to a scratch pad memory portion 84 to permit memory portion 82 to once again be utilized during a next data storage.

The second time period for which such samples are stored corresponds to a continuous seven second time period beginning three seconds before and ending four seconds after the application of cardioverting electrical energy to the atria. When atrial fibrillation is detected, cardioverting electrical energy is stored in a storage capacitor. Atrial fibrillation is then confirmed, after which it is determined if sensed activity of the heart is reliable for synchronized cardioversion. The atrial defibrillator then implements a protocol to locate an R wave with which to synchronize the deliverance of cardioverting energy. An important aspect of this protocol is the detection for a cardiac interval (the time between immediately successive R waves) which is longer than a preselected minimum time interval. This process is referred to as interval timing and is fully described in the aforementioned cross-referenced U.S. Pat. No. 5,207,219. As the atrial defibrillator implements the synchronization protocol, the memory portion 82 is addressed in a recirculating manner. When the synchronization protocol is completed, including the detection of a cardiac interval longer than the minimum interval, the addressing of the memory portion 82 is continued until four seconds after the cardioverting energy is delivered.

When the addressing of the memory portion 82 is discontinued, the contents of memory portion 82, corresponding to data collected during a period from four seconds before to four seconds after cardioverting energy delivery resides in memory portion 82. The last seven seconds of data is then transferred to the scratch pad portion 84. As a result, memory portion 82 is again available for a further data acquisition to determine if the attempted cardioversion was successful, and the scratch pad will contain data acquired continuously from three seconds before until four seconds after the application of cardioverting electrical energy to the atria. If the cardioversion was successful, the data stored in the scratch pad portion 84 is moved to memory portions 86 and 88. The data corresponding to the initial detection of atrial fibrillation (EGM1) is stored in memory portion 86 and the data corresponding to the period commencing three seconds before to four seconds after cardioversion (EGM2) is stored in memory portion 88. As a result of this selective data storage, after an atrial fibrillation episode is cardioverted, electrocardiogram samples are stored relating to the atrial fibrillation detection, relating to the successful completion of the synchronization protocol, and relating to the cardioversion.

Further, the atrial defibrillator 30 is programmable to apply a preselected number of subsequent cardioverting electrical energy pulses to the heart if previous attempts fail to successfully cardiovert the heart. If this mode is programmed, after each cardioversion attempt, a further eight second acquisition period is implemented after which the presence or absence of atrial fibrillation is determined. If atrial fibrillation is still present, the storage capacitor is once again charged. After the storage capacitor is charged, the previously-described cardioversion sequence is repeated. However, in repeating the cardioversion sequence, the electrocardiogram samples corresponding to the initial atrial fibrillation detection are retained in the scratch pad memory portion 84, but the electrocardiogram samples corresponding to the period from three seconds before to four seconds after the last attempt are written over in memory portion 84 after the next cardioversion attempt. Hence, if more than one cardioversion attempt is required to successfully cardiovert an atrial fibrillation episode or if a preselected number of cardioversion attempts is reached without successful cardioversion, the electrocardiogram samples stored for that episode will correspond to only the electrocardiograms occurring during the initial atrial fibrillation detection and before and after the last cardioversion attempt.

Since for each atrial fibrillation episode the first time period is three seconds and the second time period is seven seconds, electrocardiogram samples occurring during a total of ten seconds are stored for each atrial fibrillation episode. This permits the selective storage of electrocardiogram samples for many atrial fibrillation episodes to be retained before memory space is exhausted. The manner in which the selective data storage is implemented will now be described in greater detail, making reference to FIG. 1.

The atrial defibrillator 30 includes an implantable enclosure 32 and an implantable lead system including an intravascular lead 34 and an endocardial lead 36. The endocardial lead 36 has tip and ring electrodes 38 and respectively adapted for placement in the right ventricle 12. The intravascular lead 34 has a tip electrode 44 adapted for placement in the coronary sinus 22 or the great cardiac vein 23 and a ring electrode 46 adapted for placement in the superior vena cava 20 or right atrium 16. An alternative lead system may include separate leads for electrodes 44 and 46. This requires an additional endocardial lead (not shown in FIG. 1) adapted for placing electrode 46 in the superior vena cava 20 or the right atrium 16.

Electrodes 44 and 46 sense atrial activity of the heart and may be referred to herein as a first electrode pair. Electrodes 44 and 46 perform the additional function of applying cardioverting electrical energy across the atria 16 and 18 of the heart.

Electrodes 38 and 40 sense R waves of the heart and may be referred to herein as the second electrode pair. Electrode 44 together with either electrode 38 or electrode 40 also sense R waves of the heart and may be referred to herein as the third electrode pair. The dual sensing of the R waves between the second and third electrode pairs is performed for the purpose of reliably sensing R waves for synchronized cardioversion.

The implantable enclosure 32 includes a microprocessor 66 and a memory 80. The microprocessor controls the overall function of the atrial defibrillator 30 under software controlled by operating instructions and data stored in the memory 80. In addition to storing the operating instructions for the microprocessor 66, the memory 80 further stores electrocardiogram samples occurring during the previously-mentioned first and second time periods. To that end, the memory 80 includes the first memory portion 82, the scratch pad memory portion 84, the memory portion 86 (EGM1), and the memory portion 88 (EGM2).

Within the enclosure 32, the atrial defibrillator 30 further includes a sense amplifier 50 coupled to electrodes 38 and 40 of lead 36 to form an RV sense channel 51 and a sense amplifier 52 coupled to electrode 44 of lead 34 and to either electrode 38 or electrode 40 of lead 36 to form an RVCS sense channel 53. The sense amplifiers 50 and 52 amplify the electrocardiogram signals provided by the second and third pairs of electrodes respectively and provide R wave detectors 54 and 56 respectively with an amplified output. The R wave detectors 54 and 56 each include a threshold circuit which isolates the R waves from the amplified electrocardiograms provided by sense amplifiers 50 and 52. The outputs of the R wave detectors 54 and 56 are coupled to the microprocessor for conveying the isolated R waves to the microprocessor 66.

Another sense amplifier 58 within enclosure 32 is coupled to electrodes 44 and 46 of lead 34 to form an atrial sense channel 59. The sense amplifier 58 provides an amplified output of the electrocardiograms sensed by the first electrode pair consisting of electrodes 44 and 46. The electrocardiograms provided by sense amplifier 58 predominantly represent atrial activity of the heart 10.

The output of each of the sense amplifiers 50, 52, and 58 is coupled to an analog-to-digital converter 60 through a filter 62 and a multiplexer 64. The analog-to-digital converter 60 digitizes the electrocardiograms provided by the sense channels 51, 53 and 59 to generate electrocardiogram digital data samples. The multiplexer 64 sequentially directs the electrocardiogram signals from sense channels 51, 53 and 59 to the analog-to-digital converter 60. The electrocardiogram samples are conveyed to a direct memory access 68 which then stores the electrocardiogram samples in the memory portion 82 of memory 80.

In controlling the function of the atrial defibrillator 30, the microprocessor 66 implements an atrial fibrillation detection algorithm represented by an atrial fibrillation detector 70. The microprocessor 66 further implements the aforementioned synchronization protocol 72 and charge delivery control 74. The microprocessor 66 still further, as will be discussed hereinafter, implements a timer 73 and a counter 76.

When the atrial fibrillation detector 70 determines that the heart 10 is in atrial fibrillation, the microprocessor 66 under software control performs charge and delivery control operations pursuant to operating instructions obtained from the memory 80 to implement the charge and delivery control 74. The charge and delivery control 74 first causes the charger of circuit 75 to charge the storage capacitor therein to a selected peak voltage. The charge and delivery control 74 monitors the charging of the capacitor. When the charge delivery control 74 determines that the voltage across the storage capacitor has reached a selected peak voltage, the microprocessor, through the charge and delivery control 74, terminates the charging.

After the charging of the storage capacitor is completed, the microprocessor implements the aforementioned synchronization protocol. This confirms that R waves are being reliably sensed and that the attempted cardioversion will be performed in synchronized relation to a real R wave and one which results in a cardiac interval which is longer than a preselected minimum time interval.

Upon the successful completion of the synchronization protocol, the microprocessor causes the discharge circuit 77 which is coupled to the storage capacitor of circuit 75 to discharge a portion of its stored energy. The discharged energy is applied to electrodes 44 and 46 of the intravascular lead 34 for applying the cardioverting electrical energy to the atria 16 and 18 of the heart 10.

After the cardioverting energy is applied to the atria, the atrial defibrillator 30 determines if the cardioversion was successful in arresting the atrial fibrillation episode. If the cardioversion was not successful, the atrial fibrillation detector will once again detect for the presence of atrial fibrillation. Then, the cardioversion sequence is repeated at the same or a next higher energy level. As previously mentioned, the atrial defibrillator 30 may be programmed for repeating cardioversion attempts up to a programmable number of attempts.

The entire cardioversion sequence from original detection of an atrial fibrillation episode through successful cardioversion is initiated at periodic intervals under the control of a real time clock 90. The periodic interval is a programmable parameter of the atrial defibrillator 30 and provides periodic wakeup for the detection and cardioversion of atrial fibrillation. Atrial fibrillation is not a life-threatening malady. Hence, unlike ventricular defibrillators which must continuously detect for ventricular fibrillation, the atrial defibrillator 30 detects for atrial fibrillation at periodic intervals in order to conserve power provided by a battery 92.

Lastly, the atrial defibrillator 30 includes an RF transmitter/receiver 94 within enclosure 32. The RF transmitter/receiver includes a coiled antenna 96 for communicating through telemetry to an external programmer 100. The telemetry link provided by the RF transmitter/receiver 94 and the external programmer 100 permits the cardiologist to program the atrial defibrillator 30 with respect to its various programmable parameters and to enable the cardiologist to read from the atrial defibrillator 30 certain data which has been stored in the memory 80 including the selectively stored electrocardiogram data.

The external programmer 100 includes a receiver for receiving transmitted data from the atrial defibrillator 30 including the electrocardiogram digital samples stored in the memory portions 86 and 88. The external programmer 100 preferably initiates all transmissions from the atrial defibrillator. It further includes memory for storing the received data and a display for displaying the electrocardiograms. After the received electrocardiogram digital samples are received by the external programmer and stored in memory, the electrocardiograms may then be displayed on the display.

Figure 2:
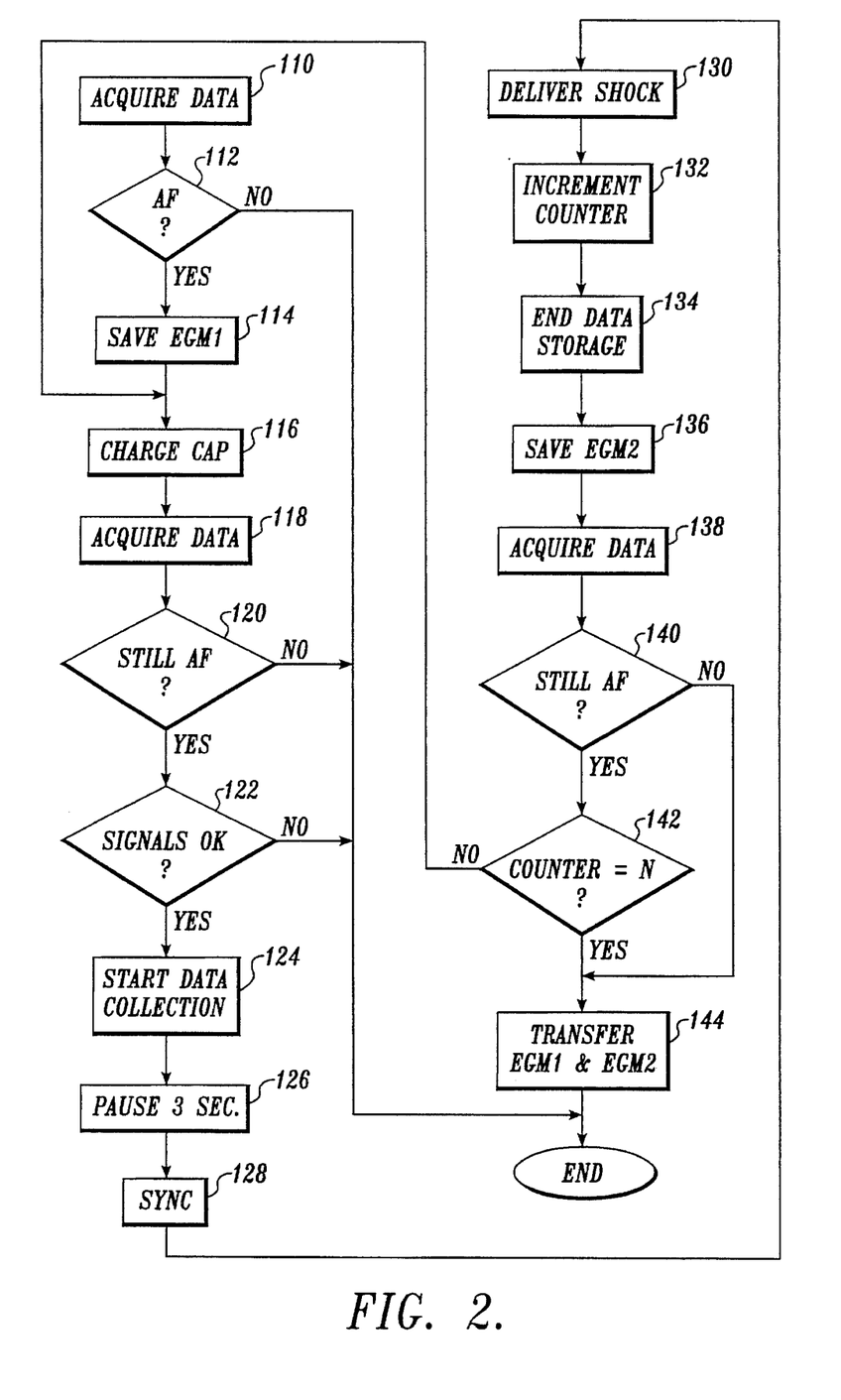
FIG. 2 is a flow diagram illustrating the manner in which the atrial defibrillator of FIG. 1 may be implemented for storing selected heart activity data related to the detection of an atrial fibrillation episode and the cardioversion of the detected atrial fibrillation episode.

The manner in which the atrial defibrillator 30 detects an atrial fibrillation episode, cardioverts the atrial fibrillation episode, and achieves selective data storage of the electrocardiogram samples will now be described with reference to the flow diagram of FIG. 2. As previously mentioned, the real time clock 90 causes the atrial defibrillator 30 to initiate detection of an atrial fibrillation episode at periodic intervals. When the atrial defibrillator 30 is to detect for an atrial fibrillation episode, the real time clock first initiates an eight second data acquisition in accordance with step 110 by activating the sense amplifiers 50, 52, and 58, the analog-to-digital converter 60, the direct memory access 68, and the memory 80. The multiplexer 64 sequentially couples the sense channels 51, 53 and 59 to the analog-to-digital converter 60 to permit the storing of digital samples of the electrocardiograms sensed by the first electrode pair of the atrial channel 59 (electrodes 44 and 46), the second electrode pair of the RV channel 51 (electrodes 38 and 40), and the third electrode pair of the RVCS channel 53 (electrode 44 and either electrode 38 or 40). The timer 73 times the eight second acquisition period and the electrocardiogram digital samples for the entire eight seconds are stored in the memory portion 82 of the memory 80. As a result, when the acquisition period is completed, the memory portion 82 will contain electrocardiogram digital samples of the electrocardiogram signals sensed by all three sense channels 51, 53 and 59 during the entire eight second acquisition period.

After completion of the eight second acquisition period, the atrial fibrillation detector 70 implements an atrial fibrillation detection algorithm by processing the data stored in the memory portion 82 to detect for atrial fibrillation in accordance with step 112. If atrial fibrillation is not detected, the activated sensing channels are deactivated until the next data acquisition is to be performed. However, if atrial fibrillation is detected in step 112, the microprocessor then in step 114 causes the last three seconds of the electrocardiogram samples stored in the memory portion 82 to be transferred into the scratch pad memory portion 84. As a result, the electrocardiogram samples of the electrocardiogram signals occurring during the last three seconds of the data acquisition period and representing the heart activity during the detection of atrial fibrillation and as sensed by all three channels 51, 53 and 59 will be retained in the scratch pad memory portion 84 of the memory 80.

After saving the first electrocardiogram samples in the scratch pad memory portion 84, the atrial defibrillator 30 through the charge delivery control 74 causes the charge and storage capacitor circuit 75 to charge the storage capacitor in accordance with step 116. As the capacitor is being charged, the charge and delivery control 74 determines if the storage capacitor of circuit 75 has been charged to a preselected peak voltage. If it has not, the charge and delivery control will continue to cause the charge and storage capacitor circuit 75 to continue charging the storage capacitor. When the charge and delivery control 74 determines that the capacitor is charged, the defibrillator will perform another eight second acquisition period in accordance with step 118. The electrocardiogram samples from all three channels 51, 53 and 59 acquired during this further eight second acquisition period are stored in the memory portion 82.

After step 118 the atrial fibrillation detector 70, in step 120, determines from the data stored in memory portion 82 if the atria are still in fibrillation. If not, the process returns. However, if the atria are still in fibrillation, the microprocessor 66 then moves to the next step 122 wherein it determines through a check signals stage 71 if the data now being stored in memory portion 82 is resulting from sense signals of sufficient quality as provided by the sense channels 51, 53 and 59.

In performing step 122, the check signals stage 71 accesses memory portion 82 to determine if the data being stored therein satisfies certain criteria. Such criteria may include amplitude range limits, periodicity and continuity. If the signals are not of good quality, but are indicative of containing noise, the process returns. If the signals are of good quality, the stage 71, in step 124, starts data collection for the synchronization protocol. The process first pauses for three seconds in step 126 to permit three seconds of data to be stored in memory portion 82 before the synchronization protocol begins in step 128. This permits the sync protocol stage 72 to access sufficient data so that if an appropriate R wave on which to synchronize is immediately found, three seconds of such data will be stored in memory portion 82 at the time the cardioverting energy is delivered.

During the synchronization protocol, the direct memory access 68 continuously addresses the memory locations of the memory portion 82 on a recirculating basis so that upon the completion of the synchronization protocol, the memory portion 82 will contain electrocardiogram digital samples of the electrocardiogram signals sensed by the channels 51, 53 and 59 during at least the last three seconds of the synchronization protocol.

The microprocessor 66 through the charge deliver control 74 in accordance with step 130 causes the discharge circuit 77 to discharge a portion of the energy stored in the storage capacitor of circuit 75 between electrodes 44 and 46 for cardioverting the atria of the heart. During this time, data from the sense channels 51, 53 and 59 continues to be stored in memory portion 82. Since electrodes 44 and 46 are used to apply the cardioverting electrical energy, sense amplifiers 52 and 58 are preferably protected by input protective circuitry well known in the art to prevent the cardioverting energy from damaging sense amplifiers 52 and 58. Even though sense amplifiers 52 and 58 are essentially blanked during this time, their outputs continue to be coupled to the analog-to-digital converter 60 by multiplexer 64 because they will still provide useful data. For example, when sense amplifier 52 is blanked, the initial blanking will provide the time in which the cardioverting energy was applied. This information can be used to confirm energy delivery and the time during the patient's cardiac cycle in which the energy was delivered to verify proper synchronization. When sense amplifiers 52 and 58 recover, they will once again provide EGM data for storage.

However, during cardioversion, the RV channel 51 is not blanked and provides useful data continuously and entirely through the energy application. This is made possible by virtue of the relatively wide spacing between first electrode pair (electrodes 44 and 46) from the second electrode pair (electrodes 38 and 40). The data provided by the RV channel 51 during this time is particularly useful to confirm that the cardioverting energy was delivered at an appropriate and safe time.

Immediately following energy discharge, the timer 73 begins to time a four second time period. During this time, the counter in step 132 is incremented to indicate the number of cardioversion attempts which have been completed for this atrial fibrillation episode.

When the timer 73 has timed the four second period beginning with the discharge of cardioverting energy, the timer 73 in step 134 causes the termination of the storing of the electrocardiogram samples in the memory portion 82. As a result, the memory portion 82 will now include electrocardiogram samples of the electrocardiogram signals provided by the sense channels 51, 53 and 59 continuously over an eight second interval beginning four seconds prior to and ending four seconds after the delivery of the cardioverting electrical energy to the atria. The data thus stored in the memory portion 82 provides the cardiologist with useful information relating to both the time at which the cardioverting electrical energy is applied to the heart relative to particular features of the heart activity such as an R wave from data from RV channel 51 and RVCS channel 53 and the return of the heart to normal sinus rhythm from data from atrial channel 59. After step 134, the microprocessor in step 136 transfers the last seven seconds of data stored in memory portion 82 into the scratch pad memory portion 84. This conditions the memory portion 82 for a further data acquisition in the next step, step 138.

In step 138, another eight second data acquisition is performed as previously described for further atrial fibrillation detection in step 140. The atrial defibrillator 30 will once again determine, from the data now stored in memory portion 82, if atrial fibrillation is still present. If the atria have been successfully cardioverted, the data stored in the scratch pad memory portion 84 is transferred in step 144 to the memory portions 86 and 88 so that, as a result of the selective data storage, the memory portion 86 will include electrocardiogram digital samples (EGM1) for electrocardiogram signals generated during the last three seconds of the first acquisition period which will relate to the initial detection of the atrial fibrillation episode of the heart, and memory portion 88 will include digital samples (EGM2) of electrocardiogram signals generated during a continuous seven second period beginning three seconds before and ending four seconds after the successful cardioversion to confirm amongst other things proper synchronization timing and successful cardioversion.

If in step 140 it is determined that the heart is still in atrial fibrillation, the microprocessor then proceeds to step 142 to determine if the number of applications of cardioverting electrical energy delivered to the heart to cardiovert the present atrial fibrillation episode equals a preselected number of applications (N). If it does, the microprocessor then performs step 144 as previously described. At this point, a predetermined number of applications of electrical cardioverting energy have been applied to the heart without successfully cardioverting the atria. At this time, the memory portion 86 will include, for this atrial fibrillation episode, electrocardiogram digital samples (EGM1) relating to the initial detection of the atrial fibrillation episode and the memory portion 88 will include electrocardiogram digital samples (EGM2) relating to a continuous seven second interval beginning three seconds before and ending four seconds after the last deliverance of cardioverting electrical energy to the atria.

If in step 142 the microprocessor 66 determines that the counter has not reached the predetermined number of counts (N), the microprocessor returns to step 116 to repeat the cardioversion process.

As a result of the foregoing, when the atrial defibrillator 30 completes its intervention for an atrial fibrillation episode, if the atria of the heart are successfully cardioverted, the memory 80 will include electrocardiogram digital samples relating to the initial detection of the atrial fibrillation in the memory portion 86, and electrocardiogram digital samples corresponding to a continuous seven second interval commencing three seconds before and ending four seconds after the last and successful application of the cardioverting electrical energy in the memory portion 88. If the heart was not successfully cardioverted, the memory 80 will contain the same information as described above in the memory portion 86. However, in the memory portion 88, the memory 80 will store electrocardiogram digital samples representing a continuous seven second interval commencing three seconds before and ending four seconds after the last, albeit unsuccessful, application of cardioverting electrical energy to the atria. Of course, as those skilled in the art will appreciate, the length of the data storage time provided may be varied without departing from the present invention.

As previously mentioned, in accordance with this preferred embodiment, only ten seconds of electrocardiogram samples are stored for each atrial fibrillation episode. While the data thus provided to the cardiologist for each atrial fibrillation episode is sufficient to provide the cardiologist with information which the cardiologist may require, numerous atrial fibrillation episodes may be accommodated by the selective data storage system of the atrial defibrillator 30.

While a particular embodiment of the present invention has been shown and described, modifications may be made, and it is therefore intended in the appended claims to cover all such changes and modifications which fall within the true spirit and scope of the invention.

What is claimed is:

1. An atrial defibrillator for applying cardioverting energy to atria of a heart and storing heart activity data related to the application of cardioverting energy comprising:

cardioverting means for applying cardioverting electrical energy to the atria of the heart;

sensing means for sensing electrical activity of the heart and generating heart activity data;

storage means for storing the heart activity data generated by said sensing means;

means for establishing a discrete continuous time interval, said discrete continuous time interval spanning a plurality of cardiac cycles of the heart;

means for causing said storage means to store generated heart activity data during said discrete continuous time interval; and means for causing said cardioverting means to apply the cardioverting electrical energy to the atria during said discrete continuous time interval.

2. An atrial defibrillator as defined in claim 1 further including telemetry means for transmitting said stored heart activity data to a non-implanted external receiver.

3. An atrial defibrillator as defined in claim 1 wherein the heart activity data include ventricular activity data and wherein said sensing means includes at least one sense channel associated with a ventricle of the heart for sensing ventricular activity of the heart and generating said ventricular activity data.

4. An atrial defibrillator as defined in claim 1 wherein the heart activity data include first ventricular activity data and second ventricular activity data and wherein said sensing means includes a first sense channel associated with a first ventricle of the heart for sensing ventricular activity of the first ventricle of the heart and generating said first ventricular activity data and a second sense channel associated with a second ventricle of the heart for sensing ventricular activity of the second ventricle of the heart and generating said second ventricular activity data.

5. An atrial defibrillator as defined in claim 4 wherein the heart activity data further include atrial activity data and wherein said sensing means further includes an atrial sense channel associated with an atrium of the heart for sensing atrial activity of the heart and generating said atrial activity data.

6. An atrial defibrillator as defined in claim 1 further including an atrial fibrillation detector to determine if the atria are in need of cardioversion, wherein the sensing means includes means associated with the atria for sensing atrial activity of the heart and generating atrial activity data, wherein the atrial defibrillator further includes means for establishing a discrete time period, said discrete time period preceeding the discrete continuous time interval and spanning a second plurality of cardiac cycles of the heart, and second means for causing said storage means to store atrial activity data generated during the discrete time period, the atrial fibrillation detector including processing means for processing the atrial activity data generated during the second discrete time period to determine if the atria are in need of cardioversion, and means for causing the storage means to retain the atrial activity data processed by the atrial fibrillation detector if the atrial fibrillation detector determines that the atria are in need of cardioversion.

7. An implantable atrial defibrillator for applying cardioverting electrical energy to the atria of a human heart in response to detection of atrial fibrillation and for storing data associated with the detection and cardioversion of the atrial fibrillation of the heart, said defibrillator comprising:

detecting means for detecting activity of the heart;

data generating means responsive to said detecting means for generating heart activity data;

atrial fibrillation detecting means responsive to detected activity of the heart for detecting atrial fibrillation of the heart;

cardioverting means responsive to the detection of atrial fibrillation for providing successive applications of cardioverting electrical energy to the atria of the heart;

memory means for storing heart activity data generated by said data generating means;

first means defining a first discrete time period corresponding to initial detection of an atrial fibrillation episode;

second means defining a second discrete time period for and corresponding to each application of cardioverting electrical energy to the atrial; and means for causing said memory means to store heart activity data generated by said data generating means during the first time period and during a last second discrete time period.

8. An atrial defibrillator as defined in claim 7 further including telemetry means for transmitting said stored selected heart activity data to a non-implanted receiver.

9. An atrial defibrillator as defined in claim 7 wherein said detecting means includes electrode means for sensing heart activity, said electrode means including plural sets of electrodes, and wherein said defibrillator further includes means for coupling said plural sets of electrodes to said memory means during said first and second discrete time periods.

10. An atrial defibrillator as defined in claim 7 wherein said memory means includes first means defining a first memory portion for storing said heart activity data generated during the first discrete time period, and a second memory portion for storing heart activity data generated during said last second discrete time period.

11. A method of applying cardioverting electrical energy to the atria of a human heart in response to detection of atrial fibrillation and for storing data associated with detection and cardioversion of an atrial fibrillation episode of the heart, said method comprising the steps of:

detecting activity of the heart and generating heart activity data during a first time period;

storing in a memory the heart activity data generated during the first time period;

processing the heart activity data stored during the first time period to determine if the atria are in fibrillation;

if the atria are in fibrillation, detecting activity of the heart and generating heart activity data during a second time period;

continuously storing the heart activity data generated during the second time period in the memory;

applying cardioverting electrical energy to the atria of the heart during the second time period; and transmitting the stored heart activity data to a non-implantable receiver.

12. A method as defined in claim 11 wherein said applying step and the last recited detecting step are repeated until one of said applications successfully cardioverts the atria, wherein each repeated last recited detecting step includes detecting activity of the heart and generating heart activity data during a respective second time period corresponding to each application of cardioverting electrical energy to the atria, and wherein the last recited storing step includes storing the heart activity data generated during each of the second time periods and retaining only the heart activity data stored during the second time period corresponding to the last one of the applications of cardioverting electrical energy.

13. A method as defined in claim 11 including the further step of preselecting a minimum interval, wherein the applying step includes detecting a heart interval longer than the preselected minimum interval and wherein the second time period includes the heart interval longer than the preselected minimum interval.

14. A method as defined in claim 11 wherein the recited storing steps include initially storing heart activity data in a first temporary memory and thereafter conveying the heart activity data to a permanent memory from the first temporary memory.

\* \* \* \* \*

UNITED STATES PATENT AND TRADEMARK OFFICE
CERTIFICATE OF CORRECTION

PATENT NO. : 5,522,850
DATED : June 4, 1996
INVENTOR(S) : Barry M. Yomtov and David P. Finch It is certified that error appears in the above-indentified patent and that said Letters Patent is hereby corrected as shown below:

On the title page:

| Item: [54] | title | "DEFIBRILLATION" should be --DEFIBRILLATOR-- |
|---|---|---|
| Col. 1 | 1 | "DEFIBRILLATION" should be --DEFIBRILLATOR-- |
| Col. 5 | 49 | insert --40-- before "respectively" |

Signed and Sealed this

Tenth Day of September, 1996

Attest:

BRUCE LEHMAN

Attesting Officer      Commissioner of Patents and Trademarks